(12) United States Patent
Bannerman

(10) Patent No.: US 6,626,929 B1
(45) Date of Patent: Sep. 30, 2003

(54) SURGICAL INSTRUMENT WITH LOCKING RATCHET APPARATUS AND METHOD

(75) Inventor: Brett Bannerman, Santa Clarita, CA (US)

(73) Assignee: Classic Wire Cut, Valencia, CA (US)

( * ) Notice: Subject to any disclaimer, the term of this patent is extended or adjusted under 35 U.S.C. 154(b) by 0 days.

(21) Appl. No.: 09/550,696

(22) Filed: Apr. 17, 2000

Related U.S. Application Data

(60) Provisional application No. 60/129,755, filed on Apr. 15, 1999.

(51) Int. Cl.[7] .............................................. A61B 17/28
(52) U.S. Cl. ...................................................... 606/205
(58) Field of Search ................................ 606/205, 206, 606/207, 208, 209; 81/338, 336, 337

(56) References Cited

U.S. PATENT DOCUMENTS

| | | | | |
|---|---|---|---|---|
| 1,310,982 A | * | 7/1919 | Davis | 606/113 |
| 1,606,497 A | * | 11/1926 | Berger | 606/113 |
| 5,209,747 A | * | 5/1993 | Knoepfler | 606/16 |
| 5,258,006 A | * | 11/1993 | Rydell et al. | 606/205 |
| 5,282,807 A | * | 2/1994 | Knoepfler | 606/143 |
| 5,300,081 A | * | 4/1994 | Young et al. | 606/143 |
| 5,304,203 A | * | 4/1994 | El-Mallawany et al. | 606/207 |
| 5,318,589 A | * | 6/1994 | Lichtman | 606/205 |
| 5,334,198 A | * | 8/1994 | Hart et al. | 606/52 |
| 5,359,993 A | * | 11/1994 | Slater et al. | 600/133 |
| 5,370,659 A | * | 12/1994 | Sakashita | 606/205 |
| 5,476,479 A | * | 12/1995 | Green et al. | 606/205 |
| 5,483,952 A | * | 1/1996 | Aranyi | 600/131 |
| 5,499,992 A | * | 3/1996 | Meade et al. | 606/170 |
| 5,603,723 A | * | 2/1997 | Aranyi et al. | 606/205 |
| 5,626,608 A | * | 5/1997 | Cuny et al. | 606/205 |
| 5,735,874 A | * | 4/1998 | Measamer et al. | 606/208 |
| 5,827,323 A | * | 10/1998 | Klieman et al. | 606/205 |
| 5,836,960 A | * | 11/1998 | Kolesa et al. | 606/170 |
| 5,893,874 A | * | 4/1999 | Bourque et al. | 606/205 |
| 5,972,021 A | * | 10/1999 | Huttner et al. | 606/210 |
| 6,042,599 A | * | 3/2000 | Huttner et al. | 606/205 |
| 6,099,550 A | * | 8/2000 | Yoon | 606/205 |
| 6,117,158 A | * | 9/2000 | Measamer et al. | 606/208 |
| 6,139,563 A | * | 10/2000 | Cosgrove et al. | 606/205 |
| 6,458,130 B1 | * | 10/2002 | Frazier et al. | 606/51 |

\* cited by examiner

*Primary Examiner*—Michael J. Milano
*Assistant Examiner*—P Roberts
(74) *Attorney, Agent, or Firm*—Richard L. Myers; Myers Dawes Andras & Sherman

(57) ABSTRACT

A surgical instrument having an elongate body includes an operative section at its distal end and a operating section at its proximal end. A pair of scissorshandles form a handle assembly in the operating section and are operable in a normal plane of operation to control the operative section. A ratchet assembly including a ratchet pawl and a series of ratchet teeth is enclosed within the handle assembly to avoid contamination by debris. The ratchet assembly can be engaged and disengaged with forces limited to the natural plane of operation; no unnatural lateral forces are required. A portion of one of the handles is moveable in the plane of operation in a first direction to engage the ratchet assembly and is moveable in the plane of operation in a second direction to disengage the ratchet assembly.

23 Claims, 3 Drawing Sheets

SURGICAL INSTRUMENT WITH LOCKING RATCHET APPARATUS AND METHOD

This is a non-provisional application claiming the priority of U.S. Provisional Application Ser. No. 60/129,755 filed on Apr. 15, 1999 and entitled Surgical Instrument with Locking Ratchet Apparatus and Method.

BACKGROUND OF THE INVENTION

1. Field of the Invention

This invention relates generally to surgical instruments having an elongate configuration with an operative section at a distal end and an operating section at a proximal end, and more specifically to such instruments which include a ratchet assembly in the operating section.

2. Discussion of the Prior Art

Many surgical instruments have a narrow, elongate shaft or tube which extends between a proximal end and a distal end. An operative section including for example the jaws of a clamp, have been disposed at the distal end and operated through the tube by an operating section, such as scissors handles, at the proximal end. These instruments are often characterized by other operative sections including clips, clamps, cutters, spreaders and other structures which perform an operative function for the instrument. The surgical instruments can also differ in the nature of the operative section at the proximal end, which is typically configured to be engaged by the surgeon to be moved to create the desired operative effect at the distal end of the instrument. The elongate tube or shaft which separate the operative section from the operating section enables the surgeon reach deeply into a body cavity through a relatively small incision.

One such instrument of the past includes an operative section in the form of a clamp having two jaws moveable relative to each other by operation of the operating section. This operating section has a pair of scissorshandles which are relatively moveable in a natural plane of operation and which carry a pair of opposing flanges each having a series of grooves. The grooves are engagable to the lock the jaws of the operative section at some predetermined relationship between a closed configuration and a open configuration. The series of grooves extend transverse to the relative movement of the handles and have peaks and valleys which extend laterally of the natural plane of movement. As a consequence, the two series of grooves can only be engaged and disengaged by bending the first and second handles in opposite lateral directions. This bending typically requires two hands or substantial strength in one hand of the user.

In the past, the two series of grooves are exposed and therefore easily contaminated with debris which can interfere with their operation. Accordingly, the surgeon has been left with a need for an elongate surgical instrument having a ratchet in its operating section which is operable with a minimum of force using a natural scissors movement, and which provides for a clean and effective operation of the instrument.

SUMMARY OF THE INVENTION

In accordance with the present invention, these deficiencies of the prior art have now been overcome with an operating section including a ratchet assembly carried by a first scissors handle having a first finger support and a second scissors handle having a second finger support. The ratchet assembly can be characterized by a ratchet pawl having a fixed relationship with the second scissors handle, and a series of ratchet teeth having a fixed relationship with an outer portion of the first finger support and pivotal relationship with an inner portion of the first finger support. In the normal operation of the scissorshandles, pressure is directed against the inner portion of the first finger support to close the scissorshandles and progressively engage the series of ratchet teeth with the ratchet pawl. This engagement of the ratchet assembly is achieved without any lateral movement of the scissors handles and totally within the normal plane of operation. In order to open the scissorshandles, normal operation exerts a pressure against the outer portion of the first scissors handle which causes the series of ratchet teeth to pivot on the first scissors handle and away from the ratchet pawl on second scissors handle. This disengagement of the ratchet assembly is achieved without any lateral movement of the scissors handles and totally within the normal plane of operation. By disengaging the ratchet assembly, the scissors handles can be further separated to open, or otherwise operate, the operative device at the distal end of the instrument.

In one aspect of the invention, the instrument is characterized by an elongate body having an axis extending between a proximal end and a distal end. An operative section is disposed at the distal end of the elongate body and a handle assembly is disposed at the proximal end of the elongate body. The handle assembly is moveable relative to the proximal end of the elongate body to operate the operative section between a first configuration and a second configuration. The handle assembly includes a first scissors handle and a second scissors handle that is moveable relative to the first scissors handle between a closed position wherein the first scissors handle has a proximate relationship with the second scissors handle and the operative device is in the first configuration, and an open position wherein the first scissors handle has a spaced relationship with the second scissors handle and the operative device is in the second configuration. A ratchet assembly is coupled to the handle assembly for progressively locking the first scissors handle relative to the second scissors handle at a predetermined position to maintain the operative device in a predetermined configuration. The ratchet assembly includes a series of ratchet teeth and a ratchet pawl which is moveable relative to the teeth to engage at least one of the teeth at the predetermined position. A finger support included in one of the first scissors handle and the second scissors handle has an outer portion that is moveable relative to the one of the first scissors handle and the second scissors handle to disengage the ratchet pawl from the series of ratchet teeth and facilitate movement of the first scissors handle toward the spaced relationship with the second scissors handle. This movement permits further operation of the operative device toward the second configuration.

In a further aspect of the invention, a method of operation is disclosed for actuating an operative device on a distal end of a surgical instrument. The method includes the steps of providing the instrument with a handle assembly including a first scissors handle, a second scissors handle and a ratchet assembly. The ratchet assembly is formed with a series of ratchet teeth and a ratchet pawl. A finger support is formed on the first scissors handle in a moveable relationship with the first scissors handle. Closing the first scissors handle relative to the second scissors handle progressively engages the series of ratchet teeth with the ratchet pawl. By moving the first finger support to disengage the ratchet pawl from the series of ratchet teeth, the first scissors handle can be opened relative to the second scissors handle.

These and other features and advantages of the invention will be discussed in greater detail with reference to certain preferred embodiments and the associated drawings.

DESCRIPTION OF PREFERRED EMBODIMENTS AND BEST MODE OF THE INVENTION

Figures 1, 2:
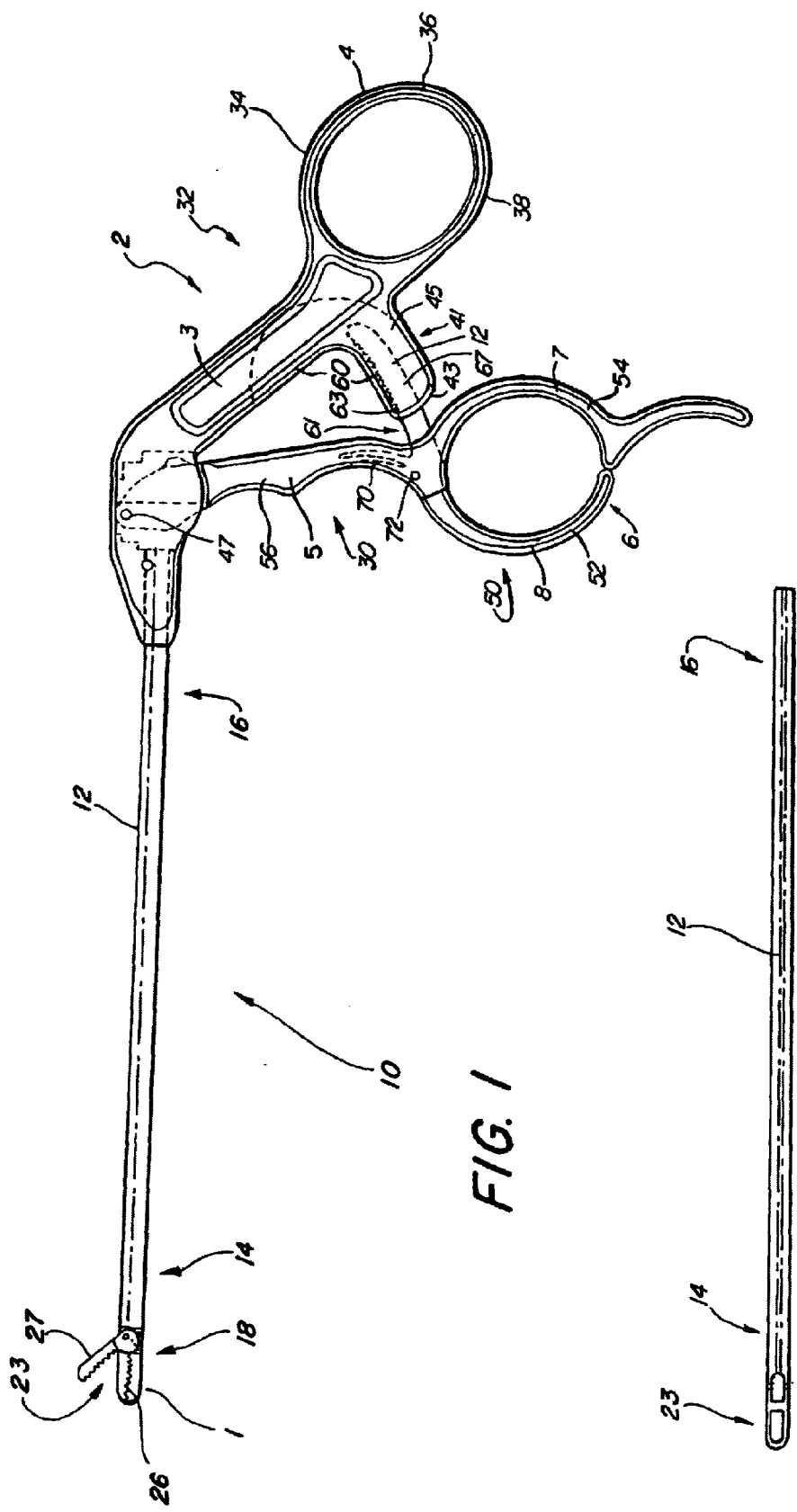
FIG. 1 is a side elevation view of one embodiment of a surgical instrument having an elongate tube with an operative section at its distal end and an operating section at its proximal end.
FIG. 2 is a top plan view of the elongate tube and operative section of FIG. 1.

A surgical instrument of the present invention is illustrated in FIG. 1 and designated by the reference numeral 10. This instrument 10 is representative of many surgical instruments which include an elongate shaft or tube 12 having a distal end 14 and a proximal end 16. The instrument 10 will typically have an operative section 18 at the distal end 14, and an operating section 21 at the proximal end 16.

The operative section may include any device performing a surgical operation such as clamping, spreading, occluding, cutting or stapling, otherwise manipulating tissue in the body of a patient. The operative section 18 in FIG. 1 is illustrated by way of example to include a clamp 23 having jaws 25 and 27 which are moveable between a generally closed configuration and the generally opened configuration illustrated in FIG. 1. In the illustrated embodiment, the jaw 26 has a fixed relationship with the tube 12 and the jaw 27 is moveable or pivotal with respect to the tube 12. In operation, the operating section 21 of the proximal end 16 is manipulated by the surgeon to move the moveable jaw 27 relative to the fixed jaw 26 and thereby adjust the clamp 23 between the opened and closed configurations.

Figure 3:
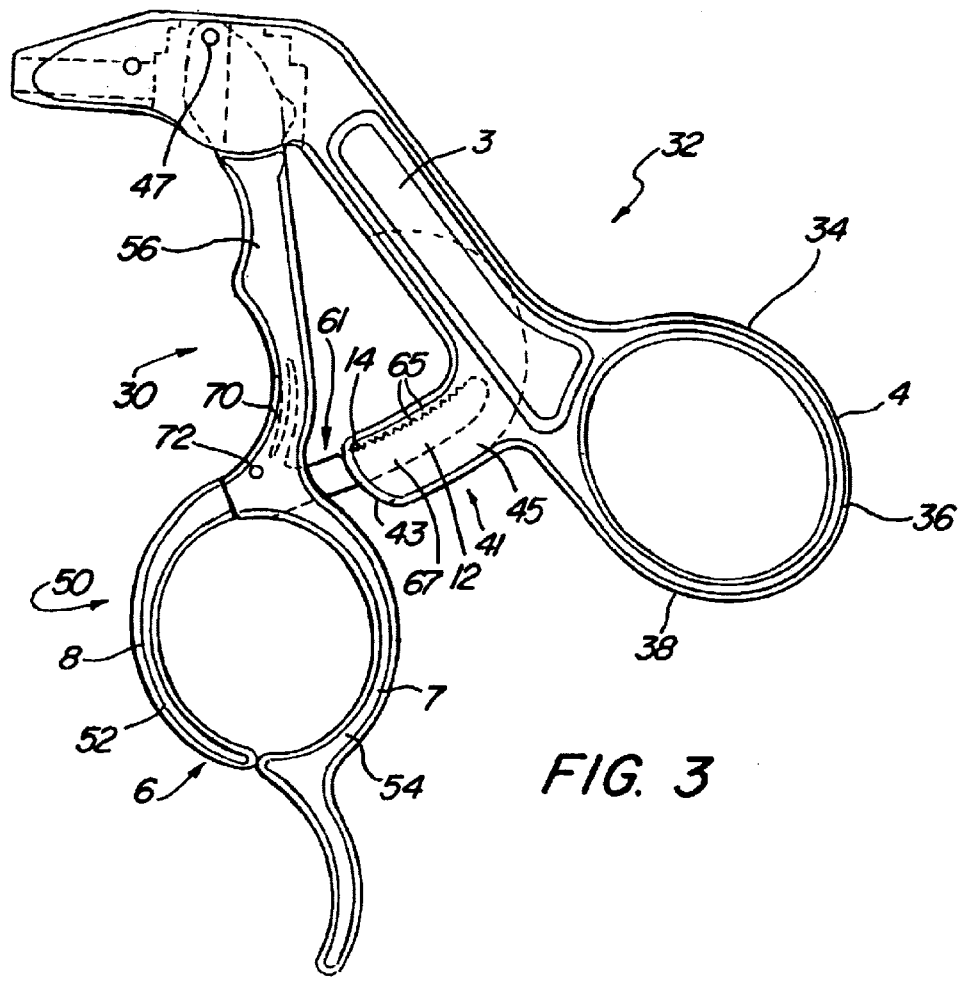
FIG. 3 is an enlarged side elevation view, partially in section, of the operating section of the FIG. 1.
Figure 4:
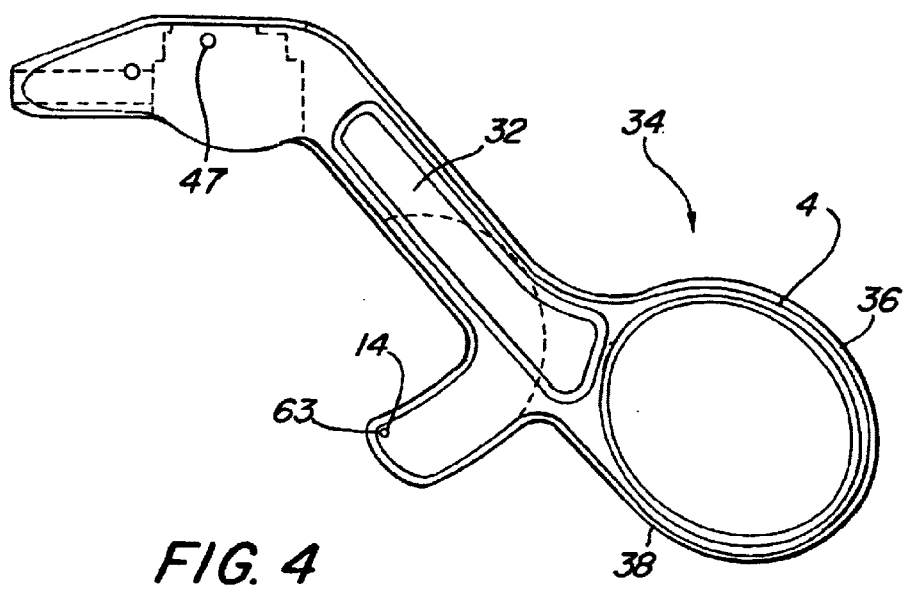
FIG. 4 is a side elevation view of a scissors handle with ratchet pawl in the operating section of the FIG. 3.

A preferred embodiment of the operating section 21 is illustrated in FIG. 1 and the enlarged view of FIG. 3. In this illustrated embodiment, the operating section 21 at the proximal end 16 of the tube 12 includes a pair of scissors handles 30 and 32. The scissors handle 32 is fixed to the tube 12 at its distal end 16 and extends proximally to a finger support or ring 34 having an outer portion 36 in a fixed, integral relationship with an inner portion 38. An inwardly extending tab 41 is carried by the scissors handle 32 and has an open end 43 which extends into a tunnel or enclosure 45 within the tab 41.

The other scissors handle 30 is pivotally mounted on the scissors handle 32 at a pivot point 47. This provides the scissors handle 30 with a moveable relationship with both the scissors handle 32 and the tube 12. At an end opposite the pivot point 47, the scissors handle 30 terminates in a finger support or ring 50 having an outer portion 52 and an inner portion 54. Between the pivot point 47 and the finger support 50, the scissors handle 30 can be constructed to form an enclosure 56.

Figure 5:
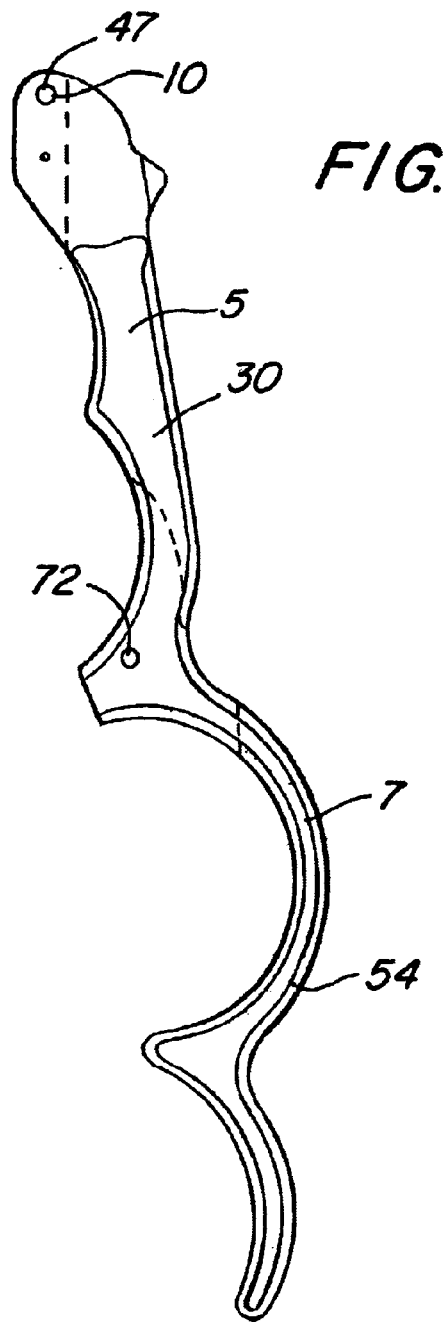
FIG. 5 is a side elevation view of another scissors handle illustrating a fixed inner portion of a finger support.
Figure 6:
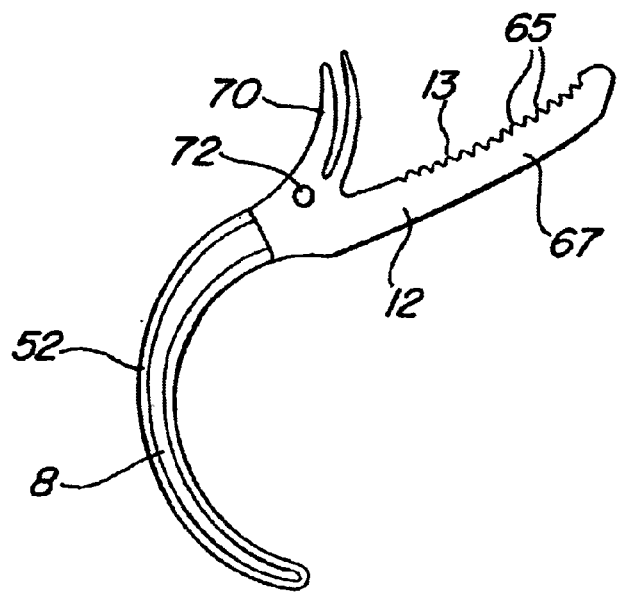
FIG. 6 is a side elevation view of a spring biased series of ratchet teeth carried by an outer portion of the finger support of FIG. 5.

In this embodiment of the operating section 21, a ratchet assembly 61 is disposed generally between the handles 30 and 32. This ratchet assembly comprises a ratchet pawl 63 which is carried by the tab 41 interiorally of the tunnel or enclosure 45. The ratchet assembly 61 also includes a series of ratchet teeth 65 which is carried by the handle 30 and cooperates with the ratchet pawl 63 on the scissors handle 32. As best illustrated in FIG. 3, the series of ratchet teeth 65 can be disposed on the circumference of a circle having a radius 66 and a center at the pivot point 47. The series of ratchet teeth 65 can be formed along an elongate projection 67 which has a generally fixed relationship with a spring member 70 and the outer section 52 of the finger support of ring 50 (FIG. 1), as illustrated in FIG. 6. The projection 67 with teeth 65, the spring member 70, and the outer portion 52 preferably have a fixed relationship and can be formed in an integral structure 71 as illustrated in FIG. 6. This structure 71 can be pivotally attached by a screw 72 to the inner portion 54 of the scissors handle 30 (FIG. 5). This provides the structure of FIG. 6 with a pivotal relationship to both the scissors handle 30 and the inner portion 54 of the finger support of ring 50.

The structure 71 is preferably mounted with the spring member 70 extending into the enclosure 56 of the handle 30, and the elongate 67 extending through the open end 43 and into the tunnel or enclosure 45 and the tab 41. With elements thus enclosed, the ratchet assembly 61 can be maintained in a generally clean environment free of any debris which might otherwise interfere with operation of the instrument 10.

With reference again to FIG. 1, it will be noted that the surgical instrument 10 is disposed in a plane 81 which is generally the plane of the page. This plane is defined generally by the tube 12 and the scissors handles 30 and 32. Importantly, it is operation of the instrument 10 totally within this plane 81 which is of particular advantage to the present invention. In a manner common to operation of scissors, the handles 30 and 32 can be moved solely within the plane 81 to operate the operative section 18 at the distal end 14 of the tube 12. Thus, with the user's thumb inserted into the finger support 34, and finger inserted into the finger support 50, the jaws 26 and 27 of the operative section 18 can be opened by separating the rings 34 and 50 and closed by moving the rings 34 and 50 into proximity. This form of operation is well known to anyone having operated a pair of scissors.

In particular it will be noted that this same movement in the plane 81, which results in the natural operation of the scissors handles 30 and 32, also operates the ratchet assembly 61. Thus, as the jaws 26 and 27 are being closed by moving the finger rings 34 and 50 into proximity, the series of ratchet teeth 65 are automatically engaged by the ratchet pawl 63 without any lateral movement of the scissors handles 30 and 32. Furthermore, the natural separation of the finger supports 34 and 50, by separating the handles 30 and 32 in the plane 81, disengages the ratchet assembly 61 so that further separation of the handles 30 and 32 can result in opening the jaws 26 and 27. Thus, operation of the instrument 10 to both open and close the jaws 26 and 27 with the aid of the ratchet assembly 61 is accomplished totally with movement in the natural plane of operation 81. No unnatural lateral forces are required or desired to either engage or disengage the ratchet assembly 61.

A more detailed analysis of this operation will show that the ratchet assembly 61 is activated as the scissors handles 30 and 32 are moved into proximity. This movement of the handles 30, 32 occurs with pressure of the user's thumb against the inner portion 38 of the ring 34 and pressure of the user's finger against the inner portion 54 of the ring 50. These two natural forces automatically engage the ratchet assembly 61 without any lateral movement of the handles 30 or 32.

The ratchet assembly 61 is disengaged when the user separates the handles 30 and 32. This is accomplished with a thumb pressure against the outer portion 36 of ring 34 and finger pressure against the outer portion 52 of the ring 50. In response to the finger pressure against the outer portion 52, the ratchet projection 67 pivots on the screw 72 away from the pawl 63 to disengage the ratchet. It again will be noted these natural separation forces on the rings 34 and 50 automatically disengage the ratchet 61 without any unnatural lateral movement of the handles 30 and 32. Once the ratchet assembly 61 is disengaged, further separation of the handles 30 and 32 can cause the jaws 26 and 27 to open.

It will be noted that the ratchet assembly 61 has an engaged state when the projection 67 is pivoted into contact with the pawl 63. The assembly 61 also has a disengaged state when the projection 67 is pivoted away from the pawl 63. It is the spring member 70, acting against the handle 30, which biases the ratchet assembly 61 to the engaged state. In this engaged state, the projection 67 in a preferred embodiment has an arcuate configuration and is generally defined along the circumference of a circle having its center at the pivot point 47.

Having described these preferred embodiments of the concept, it will now be apparent that many modifications and substitutions can be made all within the scope of the invention. For example, it will be apparent that the moveable portion 52 of the finger ring 50 can replace the inner ring portions 38 or 54, or more likely the outer ring portion 36, and alternative embodiments. In any of these positions, the moveable ring portion 52 would be pivotal in the natural plane of operation to operate the ratchet assembly 61. Other substitutions of interest might require that the pawl 63 be moveably mounted on the projection 67 while the series of ratchet teeth would be fixedly mounted within the enclosure 45.

Although the invention can be constructed in various forms, such as those discussed above, it will be apparent that the concept can be otherwise embodied to achieve the advantages discussed. Accordingly, one is cautioned not to limit the concept to these preferred embodiments, but rather to determine the scope of the invention only with reference to the following claims.

I claim:

1. A surgical instrument, including:

an elongate body having an axis extending between a proximal end and a distal end;

an operative section disposed at the distal end of the elongate body;

a handle assembly disposed at the proximal end of the elongate body, and being movable to operate the operative device between a first configuration and a second configuration at the distal end of the elongate body;

a first scissors handle included in the handle assembly;

a second scissors handle included in the handle assembly and being movable relative to the first scissors handle between a closed position wherein the first scissors handle has a proximal relationship with the second scissors handle and the operative device is in the first configuration, and an open position wherein the first scissors handle has a spaced relationship with second scissors handle and the operative device is in the second configuration;

a ratchet assembly coupled to the handle assembly for progressively locking the first scissors handle relative to the second scissors handle at a predetermined position to maintain the operative device in a predetermined configuration between the first configuration and the second configuration;

a series of ratchet teeth included in the ratchet assembly and carried by one of the first scissors handle and the second scissors handle;

a ratchet pawl included in the ratchet assembly and carried by the other of the first scissors handle and the second scissors handle, the ratchet pawl being movable relative to the series of ratchet teeth to engage at least one of the teeth at the predetermined position;

a finger support included in one of the first scissors handle and a second scissors handle; and a portion of the finger support being movable outwardly of the one of the first scissors handle and the second scissors handle to disengage the ratchet pawl from the series of ratchet teeth and permit movement of the first scissors handle toward the spaced relationship with the second scissors handle, and to permit movement of the operative device toward the second configuration.

2. The surgical instrument recited in claim 1, wherein:

a second scissors handle has a fixed relationship with the elongated body; and the first scissors handle has a pivotal relationship with the second scissors handle and the elongate body.

3. The surgical instrument recited in claim 2, wherein:

the first scissors handle is disposed distally of the second scissors handle.

4. The surgical instrument recited in claim 3 wherein the ratchet pawl is carried by the second scissors handle; and the series of ratchet teeth is pivotally mounted on the first scissors handle.

5. The surgical instrument recited in claim 4, wherein:

the portion of the finger support has a fixed relationship with the series of ratchet teeth and a pivotal relationship with the first scissors handle.

6. The surgical instrument recited in claim 5, further comprising:

a spring disposed between the finger support portion and the first scissors handle to bias the series of ratchet teeth into an engaging relationship with the ratchet pawl.

7. The surgical instrument recited in claim 6, further comprising:

portions of the first scissors handle forming an enclosure for the spring; and portions of the second scissors handle forming an enclosure for the ratchet pawl.

8. The surgical instrument recited in claim 4 wherein the first scissors handle is rotatable about a pivot point on the second scissors handle and the series of ratchet teeth is disposed on a circumference of a circle having the pivot point at a center of the circle.

9. The surgical instrument recited in claim 1 wherein the portion of the finger support is an outer portion of the finger support.

10. A method for actuating an operative device on the distal end of a surgical instrument, including the steps of:

providing the surgical instrument with a handle assembly including a first scissors handle, a second scissors handle, and a ratchet assembly disposed relative to the first scissors handle and the second scissors handle;

forming the ratchet assembly with a series of ratchet teeth progressively engagable with a ratchet pawl;

forming a finger support on the first scissors handle in the configuration of a ring; moving a first portion of the ring to close the first scissors handle relative to the second scissors handle in order to activate the operative device and to progressively engage the series of ratchet teeth with the ratchet pawl;

moving a second portion of the ring to disengage the ratchet pawl and the series of ratchet teeth; and opening the first scissors handle relative to the second scissors handle to deactivate the operative device on the distal end of the instrument.

11. The method recited in claim 10, wherein:

the second forming step includes the step of forming the finger support with a first portion and a second portion moveable relative to the first portion; and the moving step includes the step of moving the first portion of the finger support relative to the inner portion of the finger support to disengage the ratchet pawl and the series of ratchet teeth.

12. The method recited in claim 11 wherein the step of first portion of the finger support includes the step of moving an outer port of the finger support relative to the inner portion of the finger support to disengage the ratchet pawl and the series of ratchet teeth.

13. A surgical instrument, including:

an elongate member having a distal end and a proximal end;

an operative section disposed at the distal end of the elongate member and having properties for performing a surgical function at an operative site;

an operating section disposed at the proximal end of the elongate member and having properties for being operated by a user at the proximal end to control operation of the operative section at the distal end of the elongate member;

a first scissors handle and a second scissors handle included in the operating section and being moveable relative to each other in a natural plane of operation;

a finger enclosure carried by the first scissors handle;

a ratchet assembly carried by the first scissors handle and the second scissors handle, the ratchet assembly having an engaged state and a disengaged state;

the ratchet assembly being moveable between the engaged state and the disengaged state by operation of the finger enclosure of the first scissors handle in the natural plane of operation.

14. The surgical instrument recited in claim 13 wherein the ratchet assembly includes:

a series of ratchet teeth;

a ratchet pawl;

the series of ratchet teeth and the ratchet pawl being carried by the first scissors handle and second scissors handle in the operating section.

15. The surgical instrument recited in claim 14, wherein:

one of the series of ratchet teeth and the ratchet pawl is carried by the first scissors handle; and the other of the series of ratchet teeth and the ratchet pawl is carried by the second scissors handle.

16. The surgical instrument recited claim 15, wherein:

the one of the series of ratchet teeth and the ratchet pawl is pivotally mounted on the first scissors handle.

17. The surgical instrument recited in claim 16, further comprising:

first portions of the first scissors handle;

second portions of the first scissors handle having a fixed relationship with the one of the series of ratchet teeth and the ratchet pawl, the second portions of the first scissors handle being pivotal relative to the first portions of the scissors handle; whereby movement of the second portions of the first scissors handle displaces the one of the series of ratchet teeth and the pawl between the engaged state and the disengaged state of the ratchet assembly.

18. A surgical instrument, including:

an elongate member having a distal end and a proximal end;

an operative section disposed at the distal end of the elongate member and having properties for performing a surgical function at an operative site;

an operating section disposed at the proximal end of the elongate member and having properties for being operated by a user at the proximal end to control operation of the operative section at the distal end of the elongate member;

a first scissors handle and a second scissors handle included in the operating section and being movable relative to each other in a natural plane of operation;

a ratchet assembly including a series of ratchet teeth pivotally mounted on the first scissors handle and a ratchet pawl carried by the second scissors handle, the ratchet assembly having an engaged state and a disengaged state;

the ratchet assembly being movable between the engaged state and the disengaged state by operation of the first scissors handle and the second scissors handle solely in the natural plane of operation;

a support ring formed by first portions of first scissors handle and second portions of the first scissors handle, the second portions having a fixed relationship with one of the series of ratchet teeth and the ratchet pawl and being pivotal relative to the first portions; whereby movement of the second portions of first scissors handle displaces the one of the series of the ratchet teeth and the ratchet pawl between the engaged state and the disengaged state of the ratchet assembly.

19. The surgical instrument recited in claim 18, wherein:

the support ring includes an outer portion and an inner portion;

the second portions of the first scissors handle comprising the outer portion of the support ring; and the second portions of the first scissors handle being pivotal relative to the inner portion of the support ring to operate the ratchet assembly.

20. A surgical instrument, comprising:

an elongate shaft having a proximal end and a distal end;

an operative device disposed at the distal end of the elongate shaft;

a handle assembly disposed at the proximate end of the elongate shaft and including a proximal handle and a distal handle movable in a plane relative to each other to control the operative device;

a finger enclosure carried by the first handle and including a first portion and a second portion forming a substantially continuous ring;

a ratchet assembly carried by the handle assembly and movable between an engaged position and a disengaged position;

the first portion of the finger enclosure being movable in a first direction to control the operative device and to move the ratchet assembly to the engaged position; and the second portion of the finger enclosure being movable in a second direction to move the ratchet assembly to the disengaged position and to control the operative device.

21. The surgical instrument recited in claim 20 wherein the first direction and the second direction are both outwardly of the enclosure.

22. The surgical instrument recited in claim 21 wherein the first direction and the second direction are both in the plane of handle movement.

23. The surgical instrument recited in claim 22 wherein the first direction is generally opposite to the second direction.

* * * * *